United States Patent
Nabatame et al.

(10) Patent No.: US 10,121,272 B2
(45) Date of Patent: Nov. 6, 2018

(54) ULTRASONIC DIAGNOSTIC APPARATUS AND MEDICAL IMAGE PROCESSING APPARATUS

(71) Applicant: Toshiba Medical Systems Corporation, Otawara-shi (JP)

(72) Inventors: Tomio Nabatame, Otawara (JP); Yutaka Kobayashi, Nasushiobara (JP); Hiroyuki Ohuchi, Kawasaki (JP); Takashi Koyakumaru, Utsunomiya (JP); Katsuyuki Takamatsu, Yaita (JP); Taku Muramatsu, Otawara (JP); Asuka Tanigawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 68 days.

(21) Appl. No.: 15/447,773

(22) Filed: Mar. 2, 2017

(65) Prior Publication Data

US 2017/0256082 A1 Sep. 7, 2017

(30) Foreign Application Priority Data

Mar. 3, 2016 (JP) ................................ 2016-041426

(51) Int. Cl.
*G06T 11/60* (2006.01)
*G06T 7/00* (2017.01)
*G06F 3/0486* (2013.01)

(52) U.S. Cl.
CPC ............ *G06T 11/60* (2013.01); *G06F 3/0486* (2013.01); *G06T 7/0012* (2013.01); *G06T 2200/24* (2013.01); *G06T 2207/10132* (2013.01)

(58) Field of Classification Search
CPC ... G06T 11/60; G06T 7/0012; G06T 2200/24; G06T 2207/10132; G06F 3/0486
See application file for complete search history.

(56) References Cited

U.S. PATENT DOCUMENTS

| 2004/0170309 | A1* | 9/2004 | Hughes | ..................... G06T 7/30 382/128 |
| 2005/0111757 | A1* | 5/2005 | Brackett | ................ A61B 6/463 382/294 |
| 2007/0127795 | A1* | 6/2007 | Lau | ..................... G06F 17/3028 382/128 |

(Continued)

FOREIGN PATENT DOCUMENTS

| JP | 11-353327 A | 12/1999 |
| JP | 2000-175912 A | 6/2000 |

*Primary Examiner* — Maurice L. McDowell, Jr.
(74) *Attorney, Agent, or Firm* — Oblon, McClelland, Maier & Neustadt, L.L.P.

(57) ABSTRACT

According to one embodiment, the ultrasonic diagnosis apparatus includes a storing unit and processing circuitry. The storing unit is configured to store a plurality of images usable as a reference image to be referred to at the time of scanning, the plurality of images includes images corresponding to a plurality of cross sections. The processing circuitry is configured to read, when a cross section that needs to be scanned is switched in accordance with a workflow, from the storing unit one or more images registered for each of the plurality of cross sections in advance, the workflow defining a flow of procedures including scanning the plurality of cross sections. The processing circuitry is configured to display the read image as the reference image on a display.

18 Claims, 14 Drawing Sheets

(56) References Cited

U.S. PATENT DOCUMENTS

2008/0313533 A1\* 12/2008 Hoyer ................... G06F 17/211
                                                    715/243
2012/0196258 A1    8/2012  Geijsen et al.
2014/0249405 A1    9/2014  Wimer \* cited by examiner

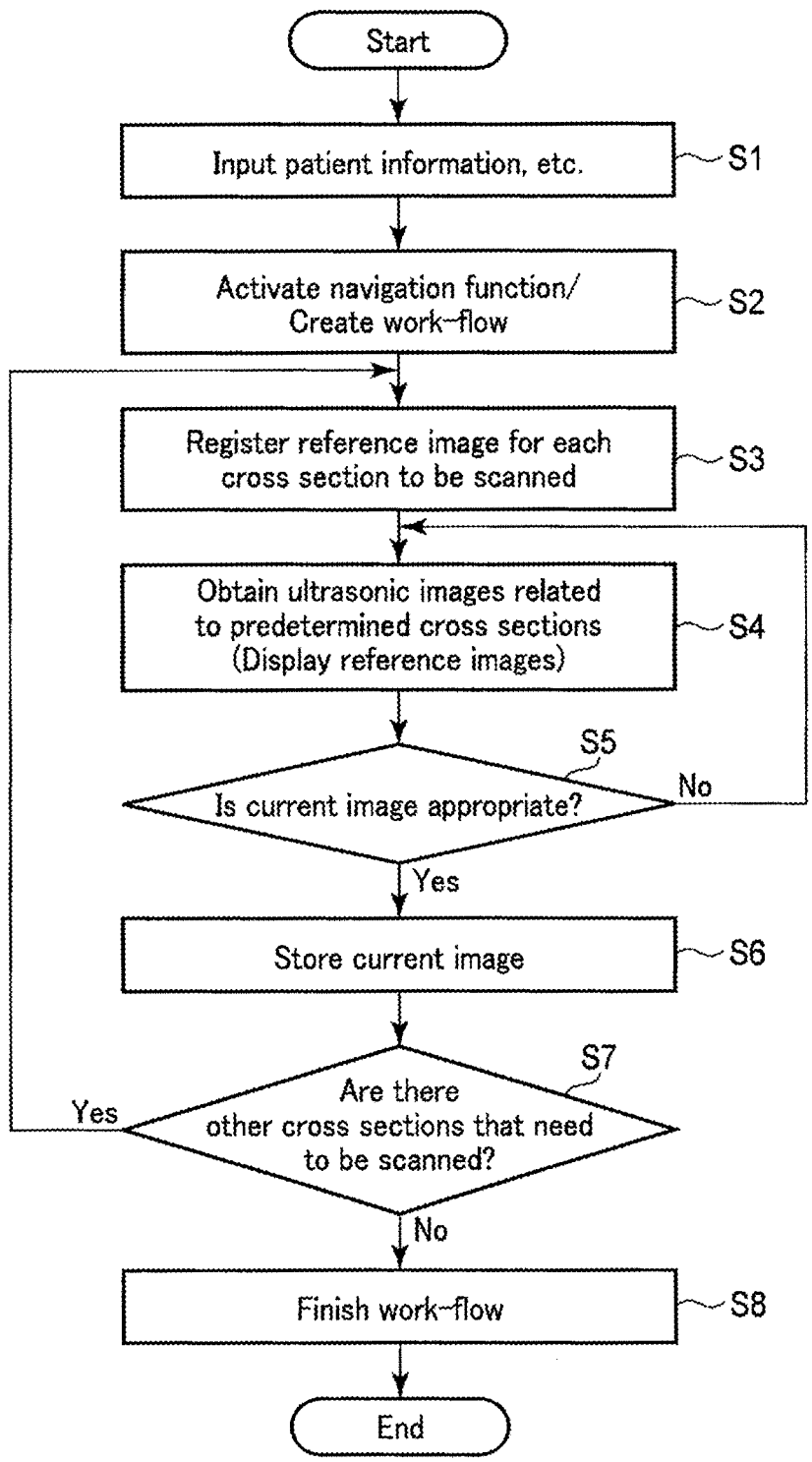
F I G. 2

| | |
|---|---|
| Exam Type | Carotid ▽ |
| ID | 0123456 |
| Last Name | Suzuki |
| First Name | Taro |
| MI | |
| | Date of Birth (yyyy/mm/dd): 1968 / 06 / 13 / 48 years |
| | Gender: ● Male  ○ Female |
| Height / Weight | 177 cm  83 kg |
| | BSA  OCCIDENTAL ▽   m2 |
| Accession No | |
| | ● In Patient  ○ Out Patient |
| Operator | ▽ |
| Insurance | ▷◁  ▷◁ |
| | Patient Comment |
| Physician | ▷ |
| Ref.Physician | ▷ |
| Department | ▽ |
| | Additional Information |

FIG. 3

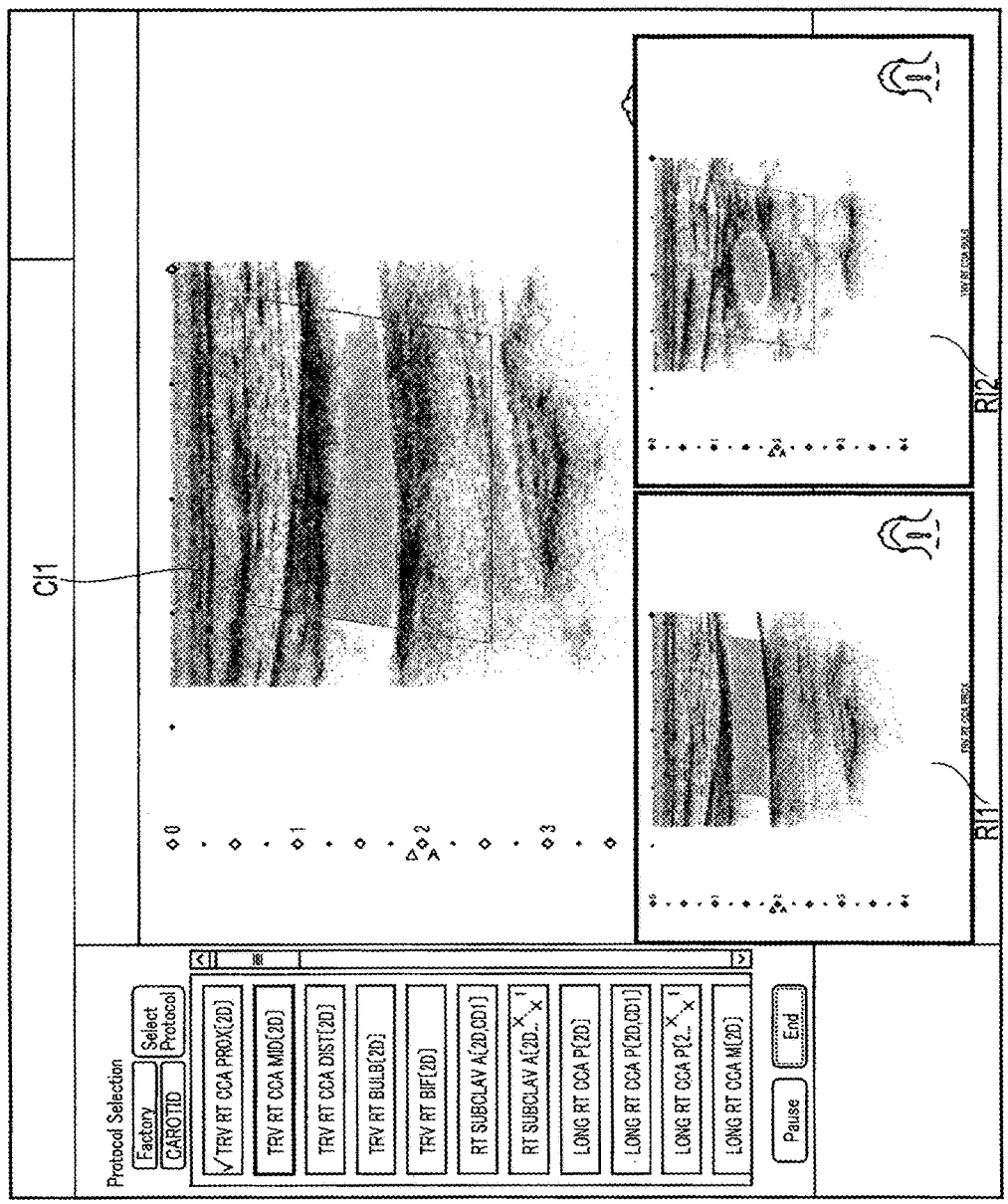
F I G. 5

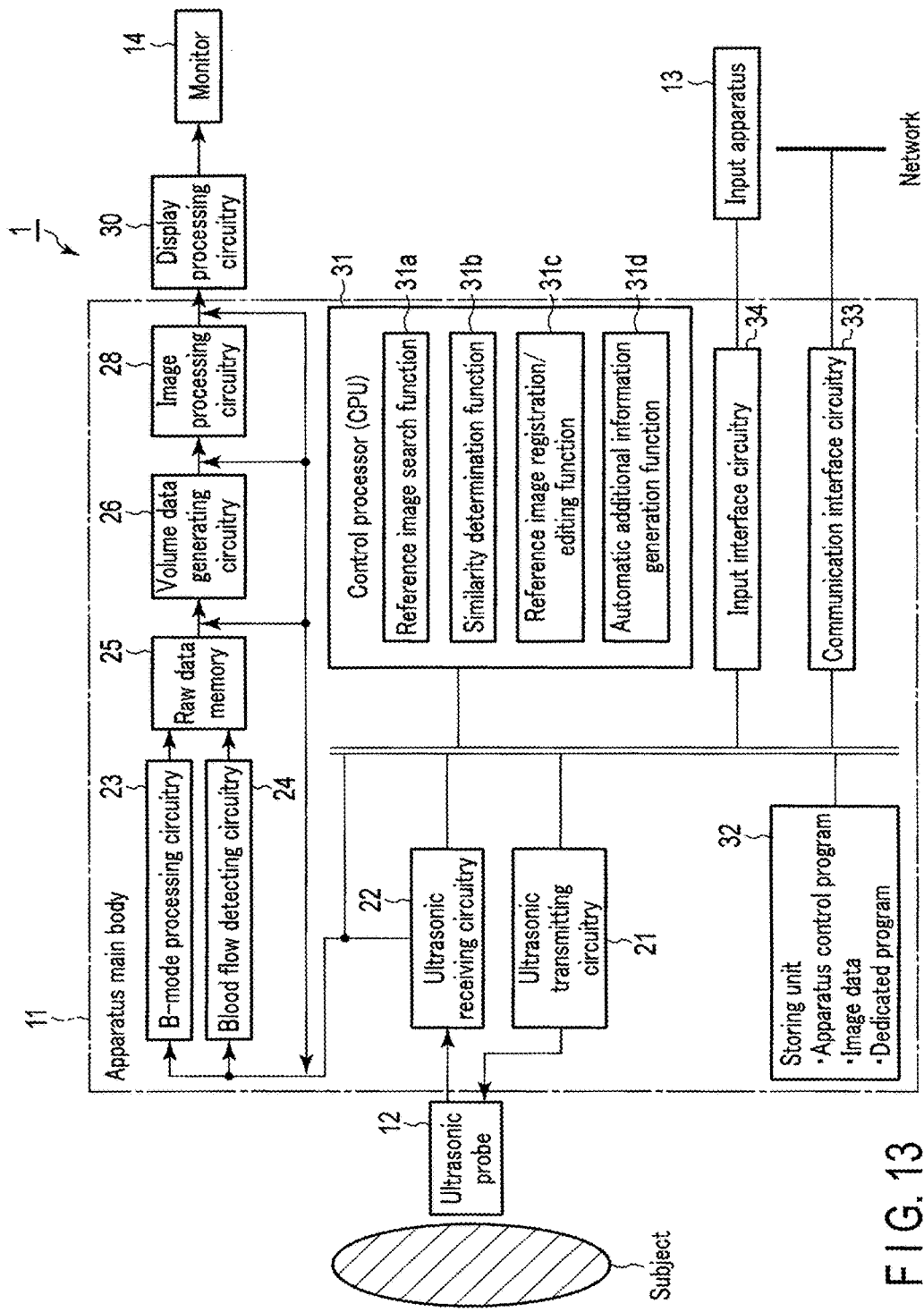
F I G. 13

ULTRASONIC DIAGNOSTIC APPARATUS AND MEDICAL IMAGE PROCESSING APPARATUS

CROSS-REFERENCE TO RELATED APPLICATIONS

This application is based upon and claims the benefit of priority from the prior Japanese Patent Application No. 2016-041426, filed Mar. 3, 2016 the entire contents of which are incorporated herein by reference.

FIELD

Embodiments described herein relate to an ultrasonic diagnosis apparatus and a medical image processing apparatus using a navigation function.

BACKGROUND

An ultrasonic diagnosis apparatus visualizes the inside of an object using ultrasonic waves, and collects biological information by transmitting an ultrasonic pulse which is generated from a transducer provided in an ultrasonic probe into the inside of the object and receiving, by the transducer, reflected waves caused by a difference of acoustic impedance among object tissues. It is possible to display videos and images in a real-time manner with a simple operation of touching a body surface with the ultrasonic probe, without concern of being exposed to radiation.

A conventional ultrasonic diagnosis apparatus usually has a function called a navigation function. This function is used for navigation to carry out measurement at a correct location by displaying a cross-sectional image of an organ that is a target of measurement, so that images necessary for diagnosis can be obtained without being missed. Using the navigation function, an operator can interactively obtain ultrasonic images necessary for examination by referring to navigation information provided by the apparatus (e.g., a cross-sectional image of an organ as a good example for which a predetermined diagnosis indicator value needs to be measured).

BRIEF DESCRIPTION OF THE DRAWING

FIG. 2 is flowchart showing a flow of the processing (navigation process) following the navigation function.

FIG. 3 is a diagram showing an input display for patient information, etc.

FIG. 5 is a drawing showing display examples of the reference image RI1, the reference image RI2, and the current image CI1.

FIG. 13 is a block diagram of the ultrasonic diagnosis apparatus according to the second embodiment.

DETAILED DESCRIPTION

Figure 1:
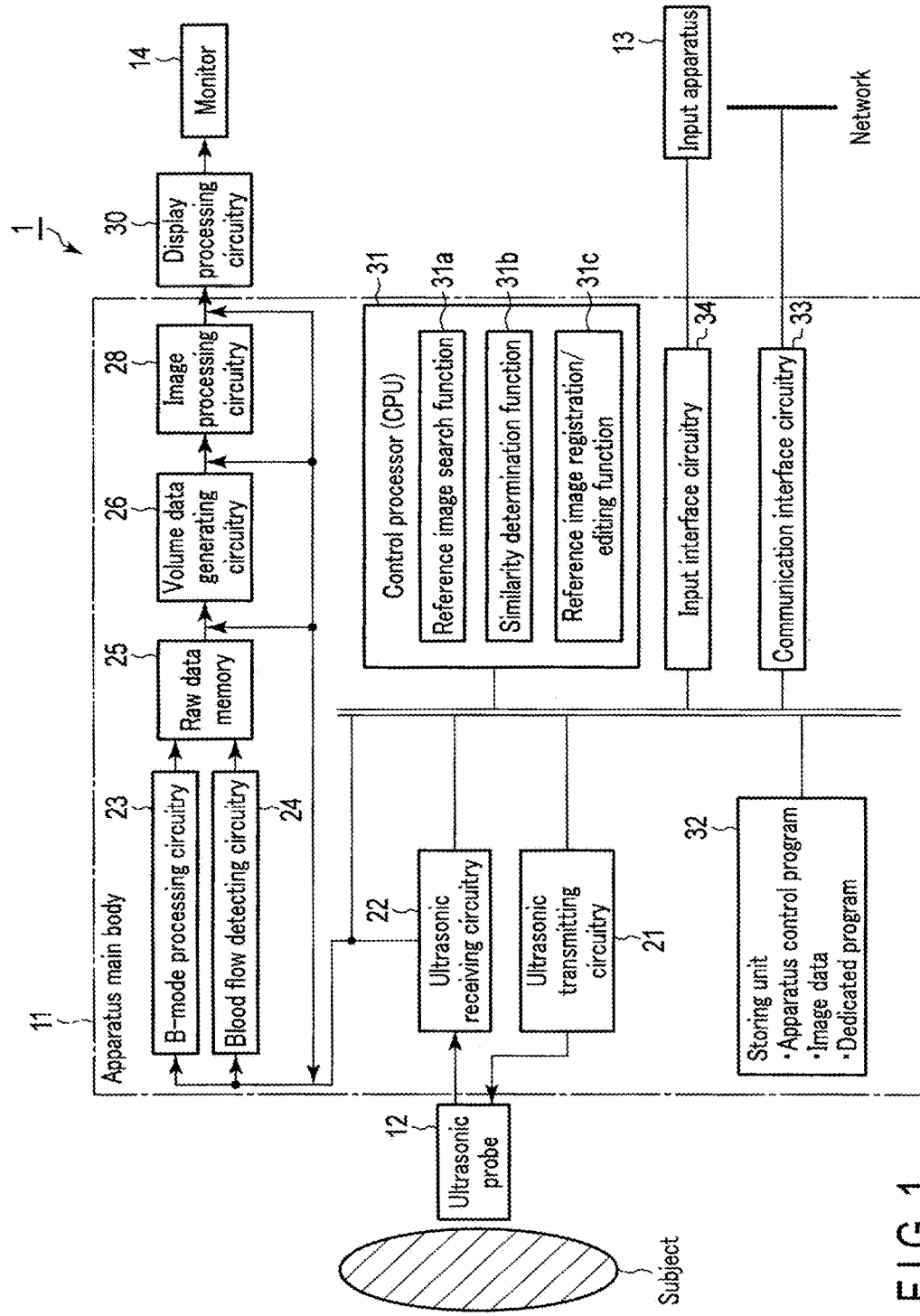
FIG. 1 is a block diagram of the ultrasonic diagnosis apparatus 1 according to the present embodiment.

However, there is still room to improve the navigation function of a conventional ultrasonic diagnosis apparatus. For example, a certain examination requires multiple measurement items and multiple specific cross-sectional images. In such an examination, there may be a case where no expected images of an organ can be found in the images that are finally stored due to lack of sufficient support from a conventional navigation function. There may be a case where a measurement is carried out at an incorrect location when measuring a distance, an area size, a time, etc. for an organ, even when a correct cross-sectional image of the organ is displayed. In those cases, it is necessary to retake the images necessary for measurement, and that causes an operator and an object a lot of physical and mental stress.

It is also necessary to add additional information, such as examination information, annotations, body marks, etc, to images collected in accordance with the workflow; if many cross-sectional images are collected, it is necessary to add additional information every time an image is stored. That causes an operator a lot of operational stress, and it is anticipated that erroneous inputs of additional information may occur.

In general, according to one embodiment, the ultrasonic diagnosis apparatus includes a storing unit and processing circuitry. The storing unit is configured to store a plurality of images usable as a reference image to be referred to at the time of scanning, the plurality of images includes images corresponding to a plurality of cross sections. The processing circuitry is configured to read, when a cross section that needs to be scanned is switched in accordance with a workflow, from the storing unit one or more images registered for each of the plurality of cross sections in advance, the workflow defining a flow of procedures including scanning the plurality of cross sections. The processing circuitry is configured to display the read image as the reference image on a display.

The ultrasonic diagnostic apparatus according to the present embodiment includes processing circuitry. The processing circuitry is configured to display a first image and a second image on a display, being arranged side by side, the first image being superimposed with first additional information. The processing circuitry is configured to store the first additional information in a storing unit, associating the first additional information with the second image as additional information of the second image, in response to an operation by an operator.

The medical image processing apparatus according to the present embodiment includes processing circuitry. The processing circuitry is configured to display a first image and a second image on a display, being arranged side by side, the first image being superimposed with first additional information. The processing circuitry is configured to store the first additional information in a storing unit, associating the first additional information with the second image as additional information of the second image, in accordance with a drag-and-drop operation from the first image to the second image.

An ultrasonic diagnosis apparatus according to the present embodiment will be described with reference to the accompanying drawings. In the description below, structural elements having substantially the same functions and configurations will be denoted by the same reference symbols, and a repetitive description of such elements will be given only where necessary.

First Embodiment

FIG. 1 is a block diagram of the ultrasonic diagnosis apparatus 1 according to the present embodiment. The ultrasonic diagnosis apparatus 1 includes an apparatus body 11, an ultrasonic probe 12 connected to the apparatus body 11, an input apparatus 13, and a monitor 14. The apparatus body 11 stores an ultrasonic transmitting circuitry 21, an ultrasonic receiving circuitry 22, a B-mode processing circuitry 23, a blood flow detection circuitry 24, a raw data memory 25, a volume data generation circuitry 26, an image processing circuitry 28, a display processing circuitry 30, a control processor (CPU) 31, a storing unit 32, a communication interface circuitry 33, and an input interface circuitry 34.

The ultrasonic probe 12 is a device (a probe) which transmits ultrasonic waves to an object, which is typically a living body, receives reflected waves from the object based on the transmitted ultrasonic waves. The ultrasonic probe 12 has an array of a plurality of ultrasonic transducers which are arranged at the distal end, a matching layer, and a backing member, etc. The ultrasonic transducers transmit ultrasonic waves in a desired direction in a scan region based on driving signals from the ultrasonic transmitting circuitry 21, and convert the reflected waves from the object into electrical signals. The matching layer is an intermediate layer which is provided for the transducers to make ultrasonic energy efficiently propagate. The backing member prevents ultrasonic waves from propagating backward form the transducers. When the ultrasonic waves are transmitted from the ultrasonic probe 12 to the object, the transmitted ultrasonic waves are sequentially reflected by a discontinuous surface of acoustic impedance of internal body tissue, and received at the ultrasonic probe 12 as an echo signal. The amplitude of this echo signal is dependent on a difference of acoustic impedance on the discontinuous surface where reflection occurs. In a case where the transmitted ultrasonic pulse is reflected by a moving blood flow, the echo is subject to a frequency shift depending on a velocity component of the moving body in the ultrasonic transmission/reception direction due to the Doppler effect.

In the present embodiment, the ultrasonic probe 12 is a one-dimensional array probe which is a plurality of ultrasonic transducers arranged along a predetermined direction. However, not limited to the example, the ultrasonic probe 12 may be a two-dimensional array probe (a probe in which a plurality of ultrasonic transducers are arranged in a two-dimensional matrix) or a mechanical 4-D probe (a probe that can performs ultrasonic scanning by mechanically stimulating an ultrasonic transducer array in its array direction and the orthogonal direction) configured to be capable of obtaining volume data.

The input apparatus 13 is a circuit connected to the apparatus body 11, and is for retrieving various instructions, conditions, setting instructions for regions of interest (ROI) from an operator, and various image condition setting instructions, etc. to the apparatus body 11, and the input apparatus is, for example, a switch, a button, a track ball, a mouse, or a keyboard, etc. An operator can perform a drag-and-drop operation, for example, for an image, etc. displayed on the monitor 14 via a mouse which acts as the input apparatus 13.

The monitor 14 displays morphological information and blood flow information of a living body as images based on video signals from the display processing circuitry 30.

The ultrasonic transmitting circuitry 21 includes, for example, a trigger generation circuit, a delay circuit, and a pulsar circuit (not shown in the drawings). The trigger generation circuit repeatedly generates trigger pulses for the formation of transmission ultrasonic waves at a predetermined rate frequency fr Hz (period; 1/fr second). The delay circuit gives each trigger pulse a delay time necessary to focus an ultrasonic wave into a beam and determine transmission directivity for each channel. The pulse circuit applies a driving pulse to the probe 12 at a timing based on the trigger pulse.

The ultrasonic receiving circuitry 22 includes, for example, an amplifier circuit, an A/D converter, a delay circuit, and an adder (not shown in the drawings). The amplifier circuit amplifies an echo signal received via the probe 12 for each channel. The A/D converter converts the amplified analog echo signal into a digital echo signal. The delay circuit determines reception directivity for the digitally-converted echo signal, and gives a delay time necessary to perform reception dynamic focus. And then, The adder performs an adding process. By the adding, the reflection component in a direction in accordance with the reception directivity of the echo signal is emphasized, and a received signal is formed as a composite beam of the ultrasonic transmission/reception in accordance with the reception directivity and the transmission directivity.

The B-mode processing circuitry 23 receives a received signal from the ultrasonic receiving circuitry 22, and performs logarithmic amplification and envelope detection processing to generate data in which signal intensity is expressed as luminance level.

The blood flow detection circuitry 24 extracts a blood flow signal from a signal received from the ultrasonic receiving circuitry 22 and generates blood flow data. The extraction of blood flow is usually performed by CFM (color flow mapping). In this case, the blood flow signal is analyzed and blood flow information, such as average velocity, variance, power, etc., is calculated as blood flow data at multiple points.

The raw data memory 25 uses multiple sets of B-mode data received from the B-mode processing circuitry 23, and generates B-mode raw data which is B-mode data on a three-dimensional ultrasonic scanning line. The raw data memory 25 uses a plurality of B-mode data sets received from the blood flow detection circuitry 24, and generates blood flow raw data which is blood flow data on a three-dimensional ultrasonic scanning line. For the purpose of noise reduction and smooth image, a three-dimensional filter may be provided after the raw data memory 25 to perform spatial smoothing.

The volume data generation circuitry 26 performs raw-voxel conversion including interpolation processing with consideration of spatial location information to generate B-mode volume data and blood flow volume data.

The image processing circuitry 28 performs certain image processing, such as volume data received from the volume data generation circuitry 26, volume rendering, multi planar reconstruction (MPR), and maximum intensity projection (MIP), for example. For the purpose of noise reduction and image smoothing, the image processing circuitry 28 may perform spatial smoothing with a two-dimensional filter provided after the image processing circuitry 28. The image processing circuitry 28 is realized when a dedicated processor, such as GPU, or a predetermined program is started and engaged by the control processor 31.

The display processing circuitry 30 performs various processing, such as corrections of dynamic range, brightness, contrast and y-curve correction, RGB conversion, etc., on a variety of image data sets generated and processed at the image processing circuitry 28. The display processing circuitry 30 is realized when a dedicated processor, such as GPU, or a predetermined program is started and engaged by the control processor 31. In the present embodiment, the volume data generation circuitry 26, the image processing circuitry 28, and the display processing circuitry 30 are together called "the image generation system".

The control processor (CPU) 31 functions as an information processing apparatus (a computer) and controls the operation at each constituent element. For example, the control processor 31 controls the ultrasonic transmitting circuitry 21, the ultrasonic receiving circuitry 22, the image processing circuitry 28, the display processing circuitry 30, etc. in accordance with transmission conditions, reception conditions, image generation conditions, image processing conditions, and display conditions, which are set in advance. Furthermore, the control processor 31 starts and engages a dedicated program stored in the storing unit 32 to realize a reference image search function 31a, a similarity determination function 31b, a reference image registration/editing function 31c, and an automatic additional information generation function 31d in the processing performed in accordance with the navigation function, which will be described later.

The storing unit 32 is composed of a memory, a SSD (solid state drive), and HDD (hard disk drive), etc. The storing unit 32 stores a program (a navigation program) for realizing the navigation function that will be described later, ultrasonic images (living body images) obtained in accordance with a scanning sequence and the navigation function, information about a connected ultrasonic probe (e.g., model and ID), diagnostic protocols, transmission conditions, reception conditions, signal processing conditions, image generation conditions, image processing conditions, display conditions, and other groups of data. Furthermore, the storing unit 32 stores a plurality of images that can be used as reference images at the time of imaging using the navigation function. Herein, a reference image is an image displayed as a good example at the time of imaging an area to be examined. As reference images, images of the patient scanned in the past, typical images of a certain disease, images of the same part of a healthy person, simulation images created using anatomical drawings, etc., for example, may be used. Furthermore, the storing unit 32 stores additional information, such as annotations and body marks added to each of the images that can be used as reference images in association with each image.

In the header of each of the images that can be used as reference images, patient information (patient ID, sex, age, height, weight, nationality), examination information (e.g., ID of examination in which the image is obtained, ID of examination in which the image is used as a reference image), an area to be examined (e.g., carotid artery, liver, heart), an image type (e.g., a B-mode image, an M-mode image, a Doppler image), a location of a cross section (e.g., a long axis cross section, a short axis cross section, a long axis two-chamber cross section, a short axis two-chamber cross section), a imaging date, and an operator, for example, are stored as additional information.

In the present embodiment, if images that can be used as reference images are ultrasonic images, the images are stored and managed as raw data. However, the present embodiment is not limited thereto; the images may be stored and managed by image data generated using raw data.

The storing unit 32 may also be used to store images in an image memory (not shown in the drawings) as needed. It is possible to transfer the data stored in the storing unit 32 to an external device via the communication interface circuitry 33. It is also possible to store the image data, etc. stored in an external server, etc. in the storing unit 32 via the communication interface circuitry 33.

The communication interface circuitry 33 is an interface related to network and connected communication devices. It is possible to connect other devices to the ultrasonic diagnosis apparatus 1 via the communication interface circuitry 33. The communication interface circuitry 33 transfers data, such as ultrasonic images obtained by the apparatus, to a different ultrasonic diagnosis apparatus and a PACS server, for example, via a network. Furthermore, it is possible to obtain desired images via the network from images that are stored in the different ultrasonic diagnosis device and the PACS server, and can be used as reference images by accessing the apparatus and server. Thus, in the present embodiment, a database of images that can be used as reference images is composed of the ultrasonic diagnosis apparatus 1, and the different ultrasonic diagnosis apparatus, and the PACS server, and the like.

If various storage devices (storing units) are connectible to the ultrasonic diagnosis apparatus 1 via the communication interface circuitry 33, images that can be used as reference images may be obtained from the storage devices storing such images via the communication interface circuitry 33. The storage devices are, for example, a connectible external HDD via an interface, such as a USB (universal serial bus), a USB memory, and a memory card.

The input interface circuitry 34 is connected to the input apparatus 13 and a new external storage device (not shown in the drawings) with wire or wirelessly, and transmits signals from the connected devices (e.g., a mouse or a keyboard) to the control processor 31.

(Navigation Function)

Next, the navigation function of the ultrasonic diagnosis apparatus 1 according to the present embodiment will be described. When the imaging operation is navigated using a flowchart called a workflow, the navigation function supports an operator by displaying a procedure (protocol) regarding imaging and measurement to be performed in a certain examination along with reference images which are switched as appropriate in accordance with the change of regions to be scanned (typically, cross sections) in accordance with the workflow.

FIG. 2 is flowchart showing a flow of the processing (navigation process) following the navigation function. The details of the processing in each step are explained as follows. In the following, a carotid artery is an example of an area to be examined to make the explanation specific. However, the navigation function is not limited to this example; it may be applicable to any area to be examined.

First, patient information (e.g., ID, name, sex, age, height, weight, nationality) and an area to be examined ("carotid" (carotid artery) as shown in FIG. 3), for example, are input via an input screen like the one shown in FIG. 3 (step S1). The control processor 31 starts a program for realizing the navigation function and reads data from the storing unit 32 to create a workflow for examining the carotid artery. The control processor 31 creates a workflow for examining the patient's carotid artery by selecting cross sections that need to be scanned during the carotid artery examination and measurement items, and listing them in a predetermined order in accordance with instructions that are input from the input apparatus 13 (step S2). The created workflow is automatically displayed in a predetermined area of a display screen in a certain format as shown in FIG. 4 (shown as workflow object WF in FIG. 4).

Next, by the reference image search function 31a, the control processor 31 compares the patient information and areas to be examined that have been input in step S1, cross sections that need to be scanned at each protocol in the workflow, and header information of the images stored in the storing unit 32 and the PACS server, etc., and searches for any matches. Images extracted as a result of the search are displayed on the monitor 14 in a predetermined format as candidates for a reference image. The operator selects images from the displayed images to be used as good examples, and registers a reference image for each cross section that needs to be scanned, using the displayed images (step S3). At this time, if a distance, an area size, or a time for the area to be examined is measured, an image in which those items are correctly expressed is registered as a reference image.

Figure 4:
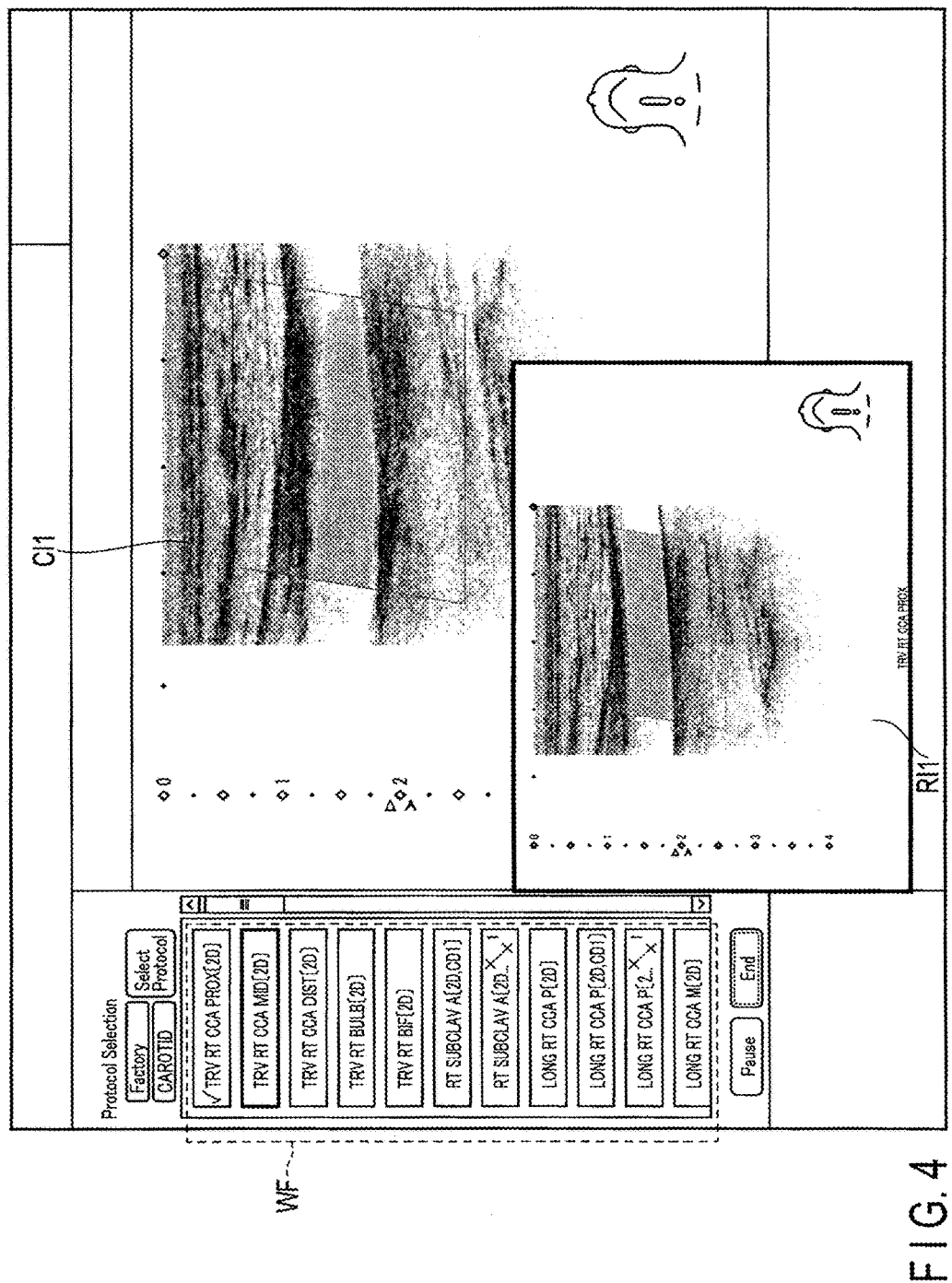
FIG. 4 is a drawing showing display examples of a workflow following the navigation function, the reference image RI1, and the current image CI1.

For example, in the first step of the workflow shown in FIG. 4, the cross section to be scanned is "TRV RT CCA PROX[2D]", and the area to be examined "carotid", sex "male", age "48", height "177", weight "83", and nationality "JP (Japan)" have been input in step S1. According to these conditions, the control processor 31 selects, from the images stored in the storing unit 32, cross-section view images which are proximal to the common carotid artery and that contain the closest matching patient information, and the selected images are displayed on the monitor 14 as candidates for a reference image for each of the cross sections to be scanned. The operator checks the displayed images, and if any of the images is registered as a reference image for scanning the cross section, the operator inputs a registration instruction via the input apparatus 13. In response to the registration instruction which is input, the control processor 31 registers the image as a reference image used in imaging "TRV RT CCA PROX[2D]". Hereafter, a reference image used as a good example is selected and registered with a similar procedure for every cross section to be scanned included in the workflow.

In step S3, more than one image may be registered as reference images. Furthermore, not only an image used as a good example but also an image showing a bad example may be adopted as a reference image. In this case, it is necessary for the operator to know whether an image displayed as a candidate or a reference image being displayed during scanning is a "good example image" or a "bad example image". Accordingly, the header information of a reference image stored in the storing unit 32 contains a distinction indicating "a good example image" or "a bad example image" for a certain examination, and it is desirable to show the information to the operator at the time of registration in step S3 and the time of scanning.

The above registration process is repeatedly performed for each cross section that needs to be scanned. Upon completion of registering reference images for all the cross sections that need to be scanned, the control processor 31 starts the examination at a predetermined timing in accordance with the workflow, and starts obtaining ultrasonic images for the cross sections to be scanned in the first step of the workflow. In the example shown in FIG. 4, the control processor 31 displays, on the monitor 14 in a predetermined format, the reference image RI1 registered as the cross section "TRV RT CCA PROX[2D]", which is first scanned in the workflow. If more than one reference image is registered, they are displayed side by side at once on the monitor 14. The control processor 31 displays an image (a current image) CI1 which is currently being scanned on the monitor 14, side by side with the reference image RI1. The operator adjusts the position of the scanning cross section, comparing the displayed reference image RI1 and current image CI1, and presses a freeze button at a predetermined timing to obtain a diagnosis image of a necessary cross section (step S4).

In step S3, for example, if both of "a good example image" and "a bad example image" are registered as reference images, the control processor 31 reads the reference image RI1 which is the good example image and the reference image RI2 which is the bad example image from the storing unit 32, and displays them on the monitor 14 in a format as shown, for example, in FIG. 5. The operator can observe both of the good example reference image RI1 and the bad example reference image RI2, and thus can determine easily and quickly by visual inspection whether an image (a current image) that is currently being scanned is for a correct cross section or a wrong cross section.

Figure 6:
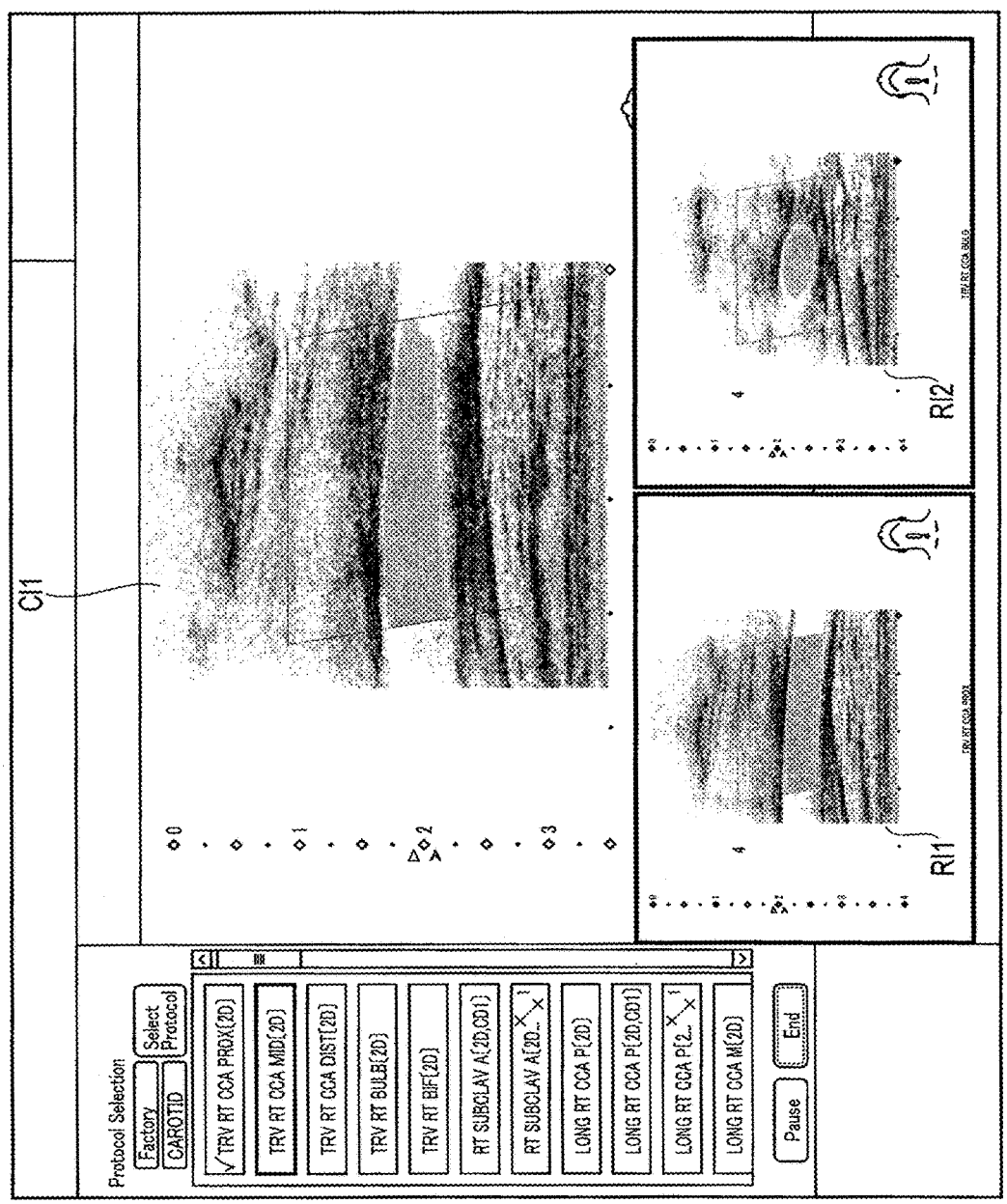
FIG. 6 is a drawing showing upside-down display examples of the reference image RI1, the reference image RI2, and the current image CI1.
Figure 7:
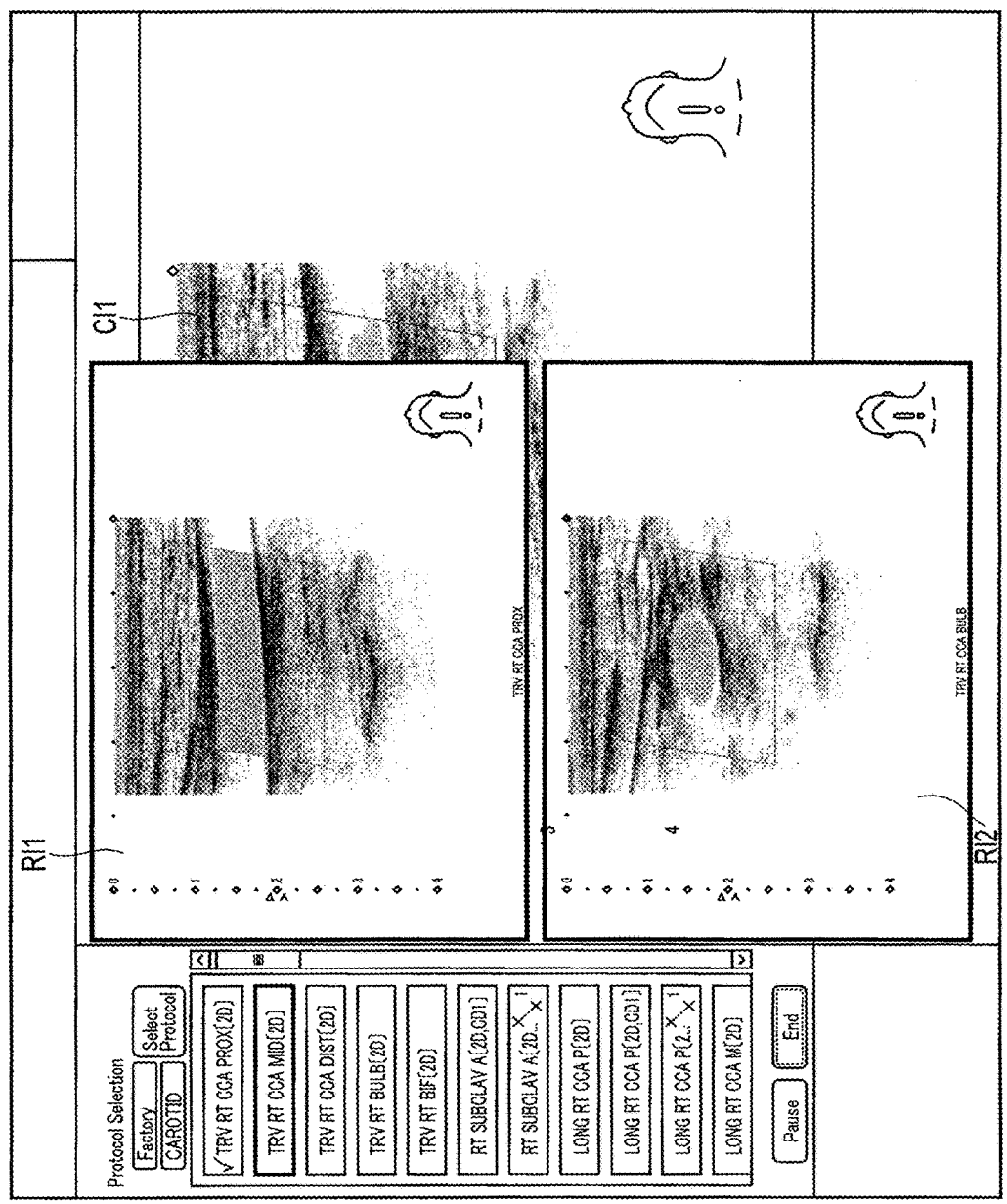
FIG. 7 is a drawing showing other display examples of the reference image RI1, the reference image RI2, and the current image CI1.

Herein, various formats can be adopted for the display of the reference images in step S4. For example, as shown in FIG. 6, if the current image CI which is currently being scanned is displayed upside down (or right-side left), the reference image RI1 and the reference image RI2 are also displayed upside down (or right-side left). Thus, it is possible to compare the current image CI with the reference image RI1 and the reference image RI2 accurately and from every angle. In the examples shown in FIGS. 5 and 6, the formats of displaying the reference image RI1 and the reference image RI2 side by side are shown. As a matter of course, it is possible to adopt a format of vertically displaying the reference image RI1 and the reference image RI2, as shown in FIG. 7. In other words, a display location, a display size and a display time for each reference image can be set as appropriate for each scanned section, operator, or patient, and the like.

Figure 8:
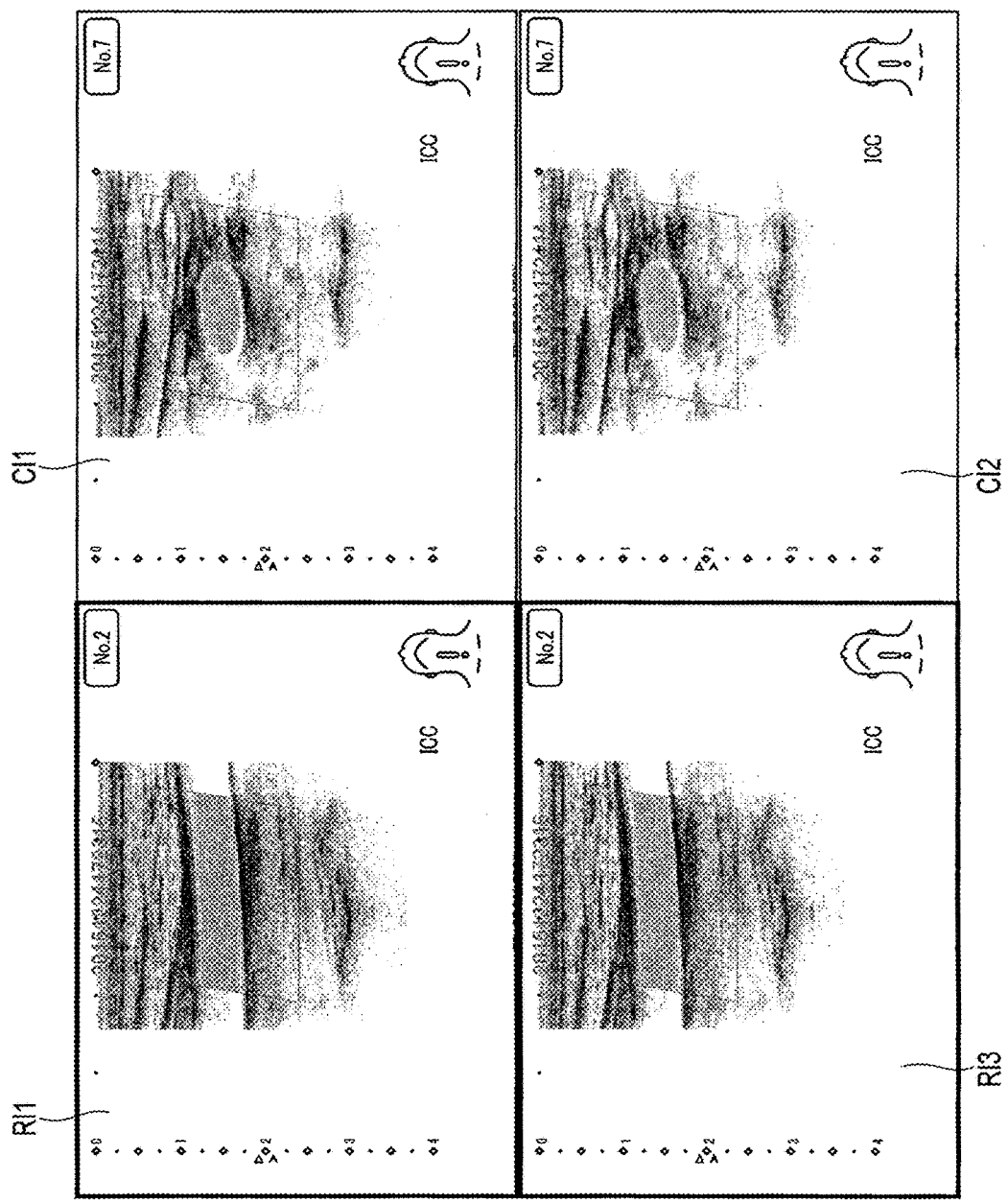
FIG. 8 is a drawing showing an example of a list display of the reference image RI1, the reference image RI2, the current image CI1, and the current image CI2.

Furthermore, in step S4, if there are multiple reference images to be referred to or multiple current images that have been obtained, it is possible to display them in a list or in thumbnails. FIG. 8 shows an example of displaying the reference image RI1 and the current image CI1 associated with each other, and the reference image RI3 and the current image CI2 associated with each other, side by side. For such an example, when an instruction to switch (shuffle) the positions of the current image CI1 and the current image CI2 is input, the control processor 31 replaces the position of the reference image RI1 with the position of the reference image RI2 in conjunction with the instruction. According to such a configuration, the operator can change the display positions of both of the current image and the reference image with one operation, while associating the current image and the reference image with each other.

Next, the control processor 31 determines, by the similarity determination function 31*b*, whether or not the current image CI1 obtained in step S4 is an image for the cross section that needs to be scanned (step S5). Specifically, the control processor 31 calculates the similarity (or dissimilarity) between the current image CI1 and the reference image RI1 that is registered as a good example by a predetermined method, such as pattern matching and frequency analysis or the like, and compares the similarity with a predetermined threshold value to determine whether or not the current image CI1 is appropriate.

The control processor 31 can use the similarity (or the dissimilarity) between the current image CI1 and the reference image RI2 that is registered as a bad example to determine whether the current image C1 is an image for the cross section that needs to be scanned. In this case, if the similarity with the reference image RI2 is higher than a predetermined threshold value, the image is of course determined to be inappropriate.

Figure 9:
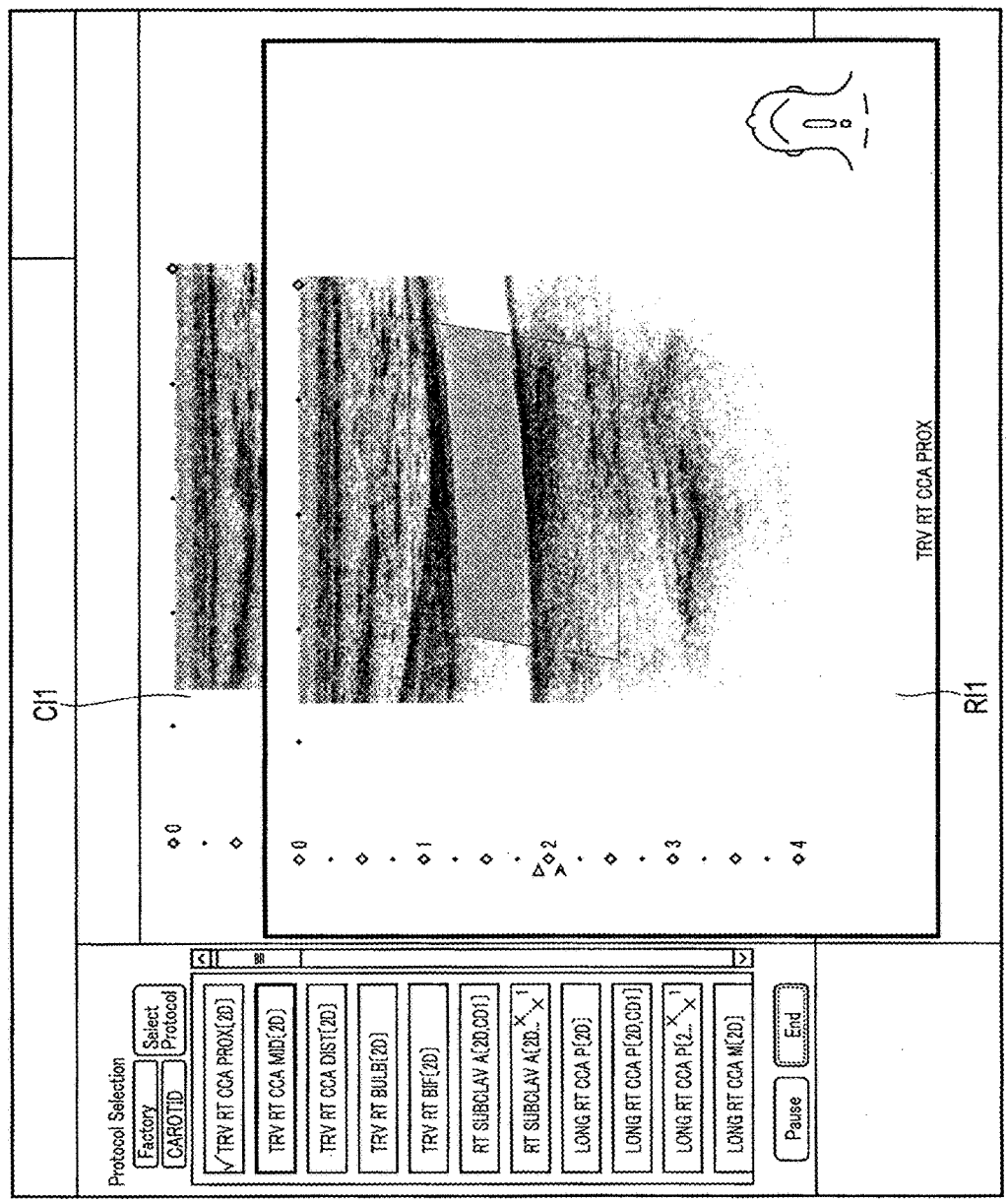
FIG. 9 is a drawing showing an example of an enlarged display of the reference image RI1.

The determination result in step S5 is notified to the operator in a predetermined format. For example, the operator is intuitively notified that the current image CI1 is appropriate as a diagnosis image of the cross section by, for example, a format such as an enlarged display of at least one of the current image CI1 and the reference image RI1 as shown in FIG. 9, or a display of the current image CI1 and/or the reference image RI1 in a temporary color or with a text indicating that the image is appropriate. With this configuration, even when the operator intends to store an image which seems appropriate, the operator can know that the image is not actually a cross-section image preferable for measurement, and the operator can start scanning again. Thus, it is possible to prevent imaging again after finishing the examination process, thereby mitigating physical and mental stress on the operator and the object.

Figure 10:
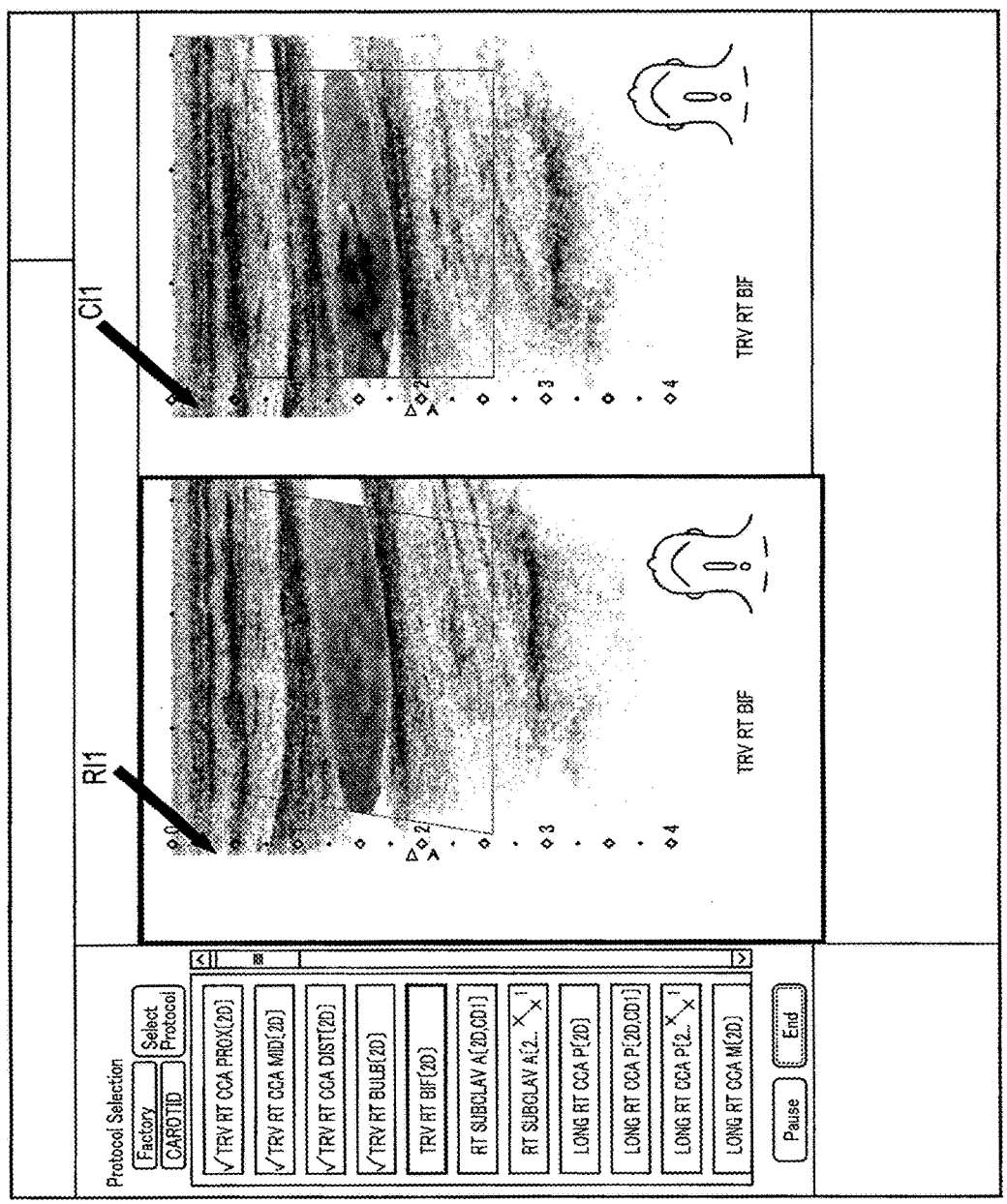
FIG. 10 is a drawing showing an example of displaying the reference image RI1 and the current image CI1 side by side under the same condition.
Figure 11:
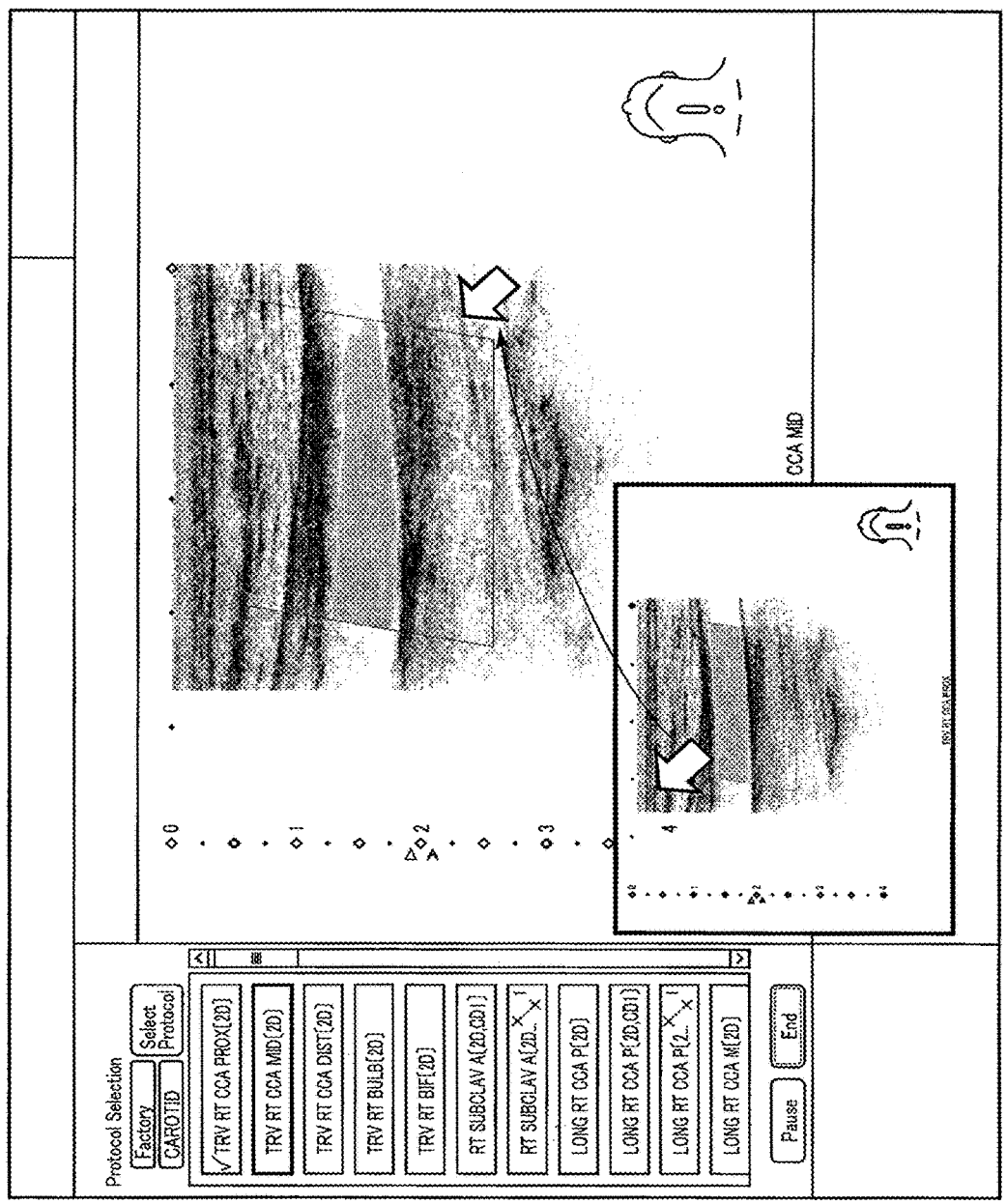
FIG. 11 is a drawing to explain an operation of selecting the current image CI1 after selecting the reference image RI1.

Next, the control processor 31 stores the current image CI1 obtained in step S4 in the storing unit 32 in response to the storing instruction from, for example, the operator (step S6). At this time, the control processor 31 may, for example, automatically print out the current image CI, the reference image RI1, and the reference image RI2 in a 2×1 layout as shown in FIGS. 5, 6, and 7, so that correspondence between the current image CI1 that is going to be stored and the reference image RI1, or non-correspondence between the current image CI1 and the reference image RI2, can be manually checked. The control processor 31 can display or print out the current image CI1 and the reference image RI1 in the same size, being arranged side by side, as shown in FIG. 10, so that manual checking can be positively prompted as to whether or not the current image CI is appropriate as a diagnosis image. Furthermore, not only the current image CI1, but also the reference image RI1 as a good example, or the reference image RI2 may be stored being associated with each other, or maintaining the aforementioned formats.

It is possible to automate the storing process in step S6. For example, when it is determined that the current image CI1 is appropriate in step S5, the control processor 31 may be caused to automatically store the current image CI1 in the storing unit 32. According to such a configuration, it is possible to omit a storing instruction, thereby mitigating operational stress on the operator.

On the other hand, for example, in step S5, if the operator erroneously inputs a storing instruction when the similarity between the good example reference image RI1 and the current image is lower than a predetermined threshold value, it is preferable that the control processor 31 displays a notification that the operator is storing the current image CI1 that does not correspond to a desired cross section, or outputs such a notification by a predetermined sound. With such a configuration, it is possible to prevent storing current images inappropriate for diagnosis.

Next, the control processor 31 determines whether there is another cross section that needs to be scanned, following the workflow, and if it is determined that "there is another cross section to be scanned", the process from step S3 to step S6 is repeated for the cross section ("Yes" in step S7). On the other hand, if it is determined that "there is no other cross section to be scanned", the control processor 31 finishes the process following the workflow ("No" in step S7) (step 8).

An example of the navigation process according to the present embodiment is explained as in the foregoing, but the navigation process is not limited thereto; the navigation process may be modified in various ways. Some modifications will be described below. Each of the modifications, which will be described below, can of course be combined with each other.

(Modification 1)

The above-described navigation function is beneficial when scanning is required for progress observation, or when a different way of scanning is required in accordance with diseases.

In the following, an examination for progress observation of liver cirrhosis will be explained as an example. For the case of progress observation, when registering a reference image in step S3, an image of a patient's liver taken in the past (e.g., an image recently taken), or a reference image used in a previous examination, is registered as a reference image for this time. Such registration can be realized by using "previous examination ID", for example, as a search condition in the step S3. The operator can perform scanning at a higher precision compared to conventional scanning by using a previous image of the same patient or a good example image used in the previous imaging as a reference image in the current imaging.

(Modification 2)

In the above-described navigation function, an operation of selecting a current image after selecting by a cursor a reference image used as a good example causes the display conditions for the current image (e.g., Acc Power, dynamic range) to be set the same as the display conditions for the reference image. By the same operation, an scanning mode (e.g., an M-mode, a contrast harmonic imaging (CHI) mode, a tissue harmonic imaging (THI) mode, a pulse Doppler mode, a continuous wave Doppler mode) may be automatically switched in accordance with the displayed reference image. In this case, after performing B-mode scanning in accordance with the workflow, for example, if the next reference image is an M-mode image, selecting the current image after selecting the M-mode image (a reference image) by a cursor causes the control processor 31 to switch the imaging mode from a B-mode to an M-mode. According to such a configuration, it is possible to change display conditions and imaging modes by an operation of selecting images, thereby mitigating operational stress on the operator.

(Modification 3)

In step S3, as described above, the search for the storing unit 32 and the PACS server is performed based on the patient information and the area to be examined that are input in step S1, and images that match conditions from the images usable as reference images are selected. However, the embodiment is not limited thereto, and a desired image can be extracted using search conditions at the operator's discretion, such as an area to be examined only or a disease name.

(Modification 4)

In the foregoing embodiment, an example is described in which the images stored in the storing unit 32 and the PACS server, etc., on hospital internal network are searched and the extracted images are used to register a reference image for each cross section that needs to be scanned. However, the embodiment is not limited thereto; for example, images on a server of an external network or on a website, images introduced at an institute, and images in a textbook can be used to register a reference image for each cross section that needs to be scanned. In other words, images used as a reference image can be freely selected and edited on a user side using the reference image registration/editing function 31c, and can be registered as reference images. The images registered in such a manner as reference images are stored in the storing unit 32, or the like, as a matter of course, and managed in a database as images usable as reference images.

(Modification 5)

As described in Modification 4, in the ultrasonic diagnosis apparatus 1, it is possible to expand the range of images that can be used as reference images by adding desired images to the database using the reference image registration/editing function 31c. It is desirable to configure the control processor 31 to be capable of classifying the images in the database with respect to properties, such as patient information (e.g., sex, age, height, weight, nationality), an area to be examined, and a disease name, and capable of outputting, for example, a list indicating which of images of a particular property are lacking. The operator can realize the navigation process using more appropriate reference images by adding images of a particular property that are lacking.

(Modification 6)

Each of the images stored and managed in the database is associated with unique additional information (e.g., annotations and body marks). With the reference image registration/editing function, it is possible to collectively edit all the additional information for images in the database having identical properties.

Figure 12:
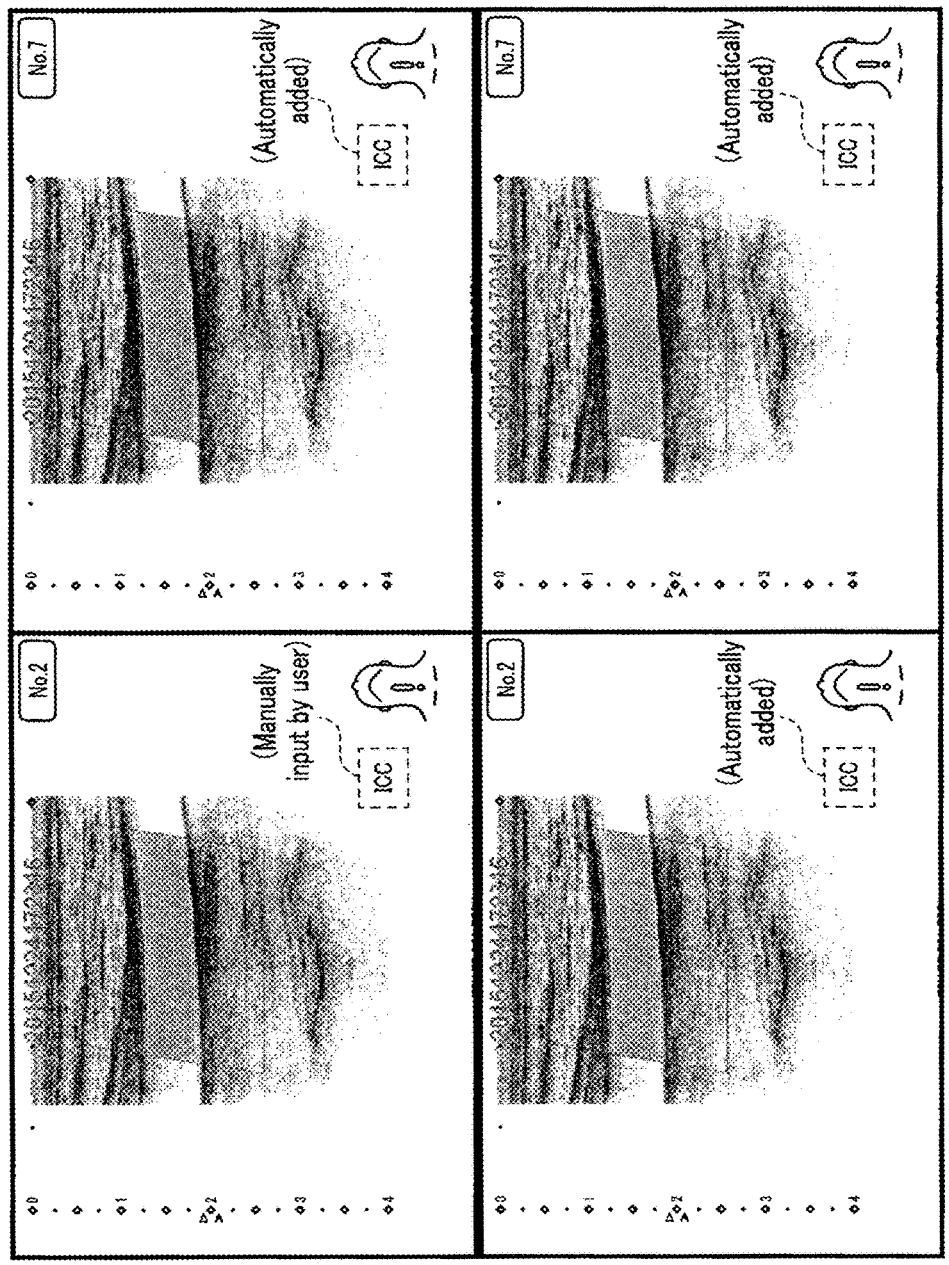
FIG. 12 is a drawing to explain an operation of adding annotations to images having the same properties.

Suppose searching the database for an image having the property "carotid artery" is performed. In this case, as shown in FIG. 12, when the annotation "ICC" is added to any of the extracted images (the top left image in the example shown in FIG. 12), the same annotation "ICC" is also added to the other images extracted for the same property. Annotated additional information is stored and managed while being associated with a corresponding image. Accordingly, if any of these images is later read and displayed by itself, it will be annotated as "ICC". In a case where any unnecessary annotation is added in common, images having the same property are extracted so that editing such as changes and deletion can be made.

According to the configuration described above, it is possible to collectively edit all together additional information, such as texts (e.g., annotations) and body marks, for images having identical properties in the database, thereby mitigating operational stress on the operator.

(Advantageous Effects)

According to the above-described configuration, when the scanning work is navigated in a particular order using the navigation function, it is possible to switch a reference image as appropriate in accordance with a change of a region to be scanned. Thus, even in an examination during which multiple cross sections are scanned and multiple items are measured, it is possible to support the scanning work with a use of a navigation image corresponding to each cross section or measurement item. As a result, it is possible to prevent forgetting to scan a cross section that needs to be scanned and carrying out measurement at a wrong location, thereby mitigating physical and mental stress on an operator and an object.

Second Embodiment

FIG. 13 is a block diagram of the ultrasonic diagnosis apparatus according to the second embodiment. By comparison, the ultrasonic diagnosis apparatus is different from the configuration shown in FIG. 1 in that "the automatic additional information generation function 31d" is added to the control processor 31.

Figure 14:
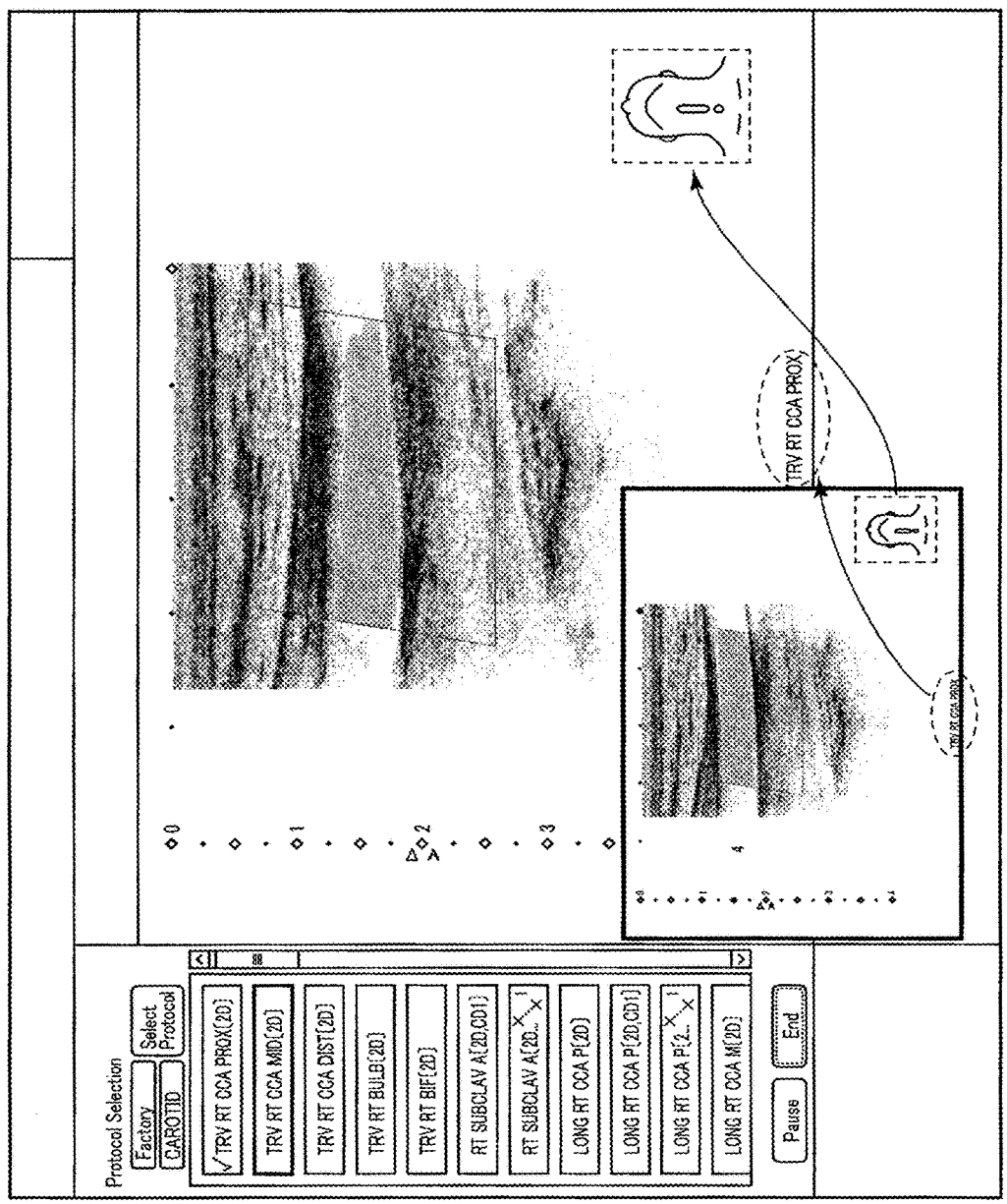
FIG. 14 is a drawing showing a drag-and-drop operation from a reference image to a current image.

Generally, additional information, such as annotations and body marks, are superimposed on an ultrasonic image when being displayed. The control processor 31 automatically copies and stores the additional information superimposed on the reference image at a discretionary timing in response to the drag-and-drop operation from the reference image to the current image as shown in FIG. 14 (the automatic additional information generation function 31d). The additional information may be copied and pasted, or cut and pasted by the drag-and-drop operation.

More specifically, the control processor 31 operates in a manner as described below. The additional information superimposed on the reference image is stored and managed while being associated with the reference image and the layout information. Herein, the layout information is information indicating a location at which each additional information is arranged on the screen.

The control processor 31 copies the additional information and the layout information that are associated with the reference image in response to the drag-and-drop operation from the reference image to the current information, and automatically stores the copied information being associated with the current image. The control processor 31 displays additional information at a predetermined position on the screen, using the copied additional information and layout information. The annotations and body marks displayed as the additional information of the current image are editable as needed (change, addition, and deletion of content, or change of position, size, and colors). Accordingly, after copying the additional information of the reference image at an approximate position by the drag-and-drop operation, the operator can make minor adjustments to the position using a mouse, etc., to make the copied additional information as additional information of the current image.

It is not always necessary to copy the layout information in the present embodiment. For example, the annotations and body marks on the reference image may be copied as additional information of the current image by adjusting the position by drag-and-dropping each of the annotations and body marks to the current image.

The automatic additional information generation function according to the present embodiment is typically performed at the same time as the storing at step S6 shown in FIG. 2, for example, but is not limited thereto; the function may be performed at a discretionary timing. Furthermore, the function is applicable to a case where two ultrasonic images are arranged side by side, not on the assumption of the navigation function, and additional information displayed being associated with one of the ultrasonic images and superimposed thereon is copied as additional information as the other ultrasonic image.

The automatic additional information generation function according to the present embodiment is not limited to ultrasonic images, and it is applicable to copying additional information between two images obtained by a modality other than an ultrasonic diagnosis apparatus (e.g., an X-ray CT apparatus, a magnetic resonance imaging apparatus, an X-ray diagnosis apparatus, PET, SPECT, etc.), or copying additional information between images obtained by different modalities.

According to the above-described configuration, the operator can easily and quickly copy the additional information, such as annotations and body marks, of a first image (e.g., a reference image) to a second image (e.g., a current image) only by performing a drag-and-drop operation. As a result, it is possible to prevent unsuccessful copying and miscopying and to contribute to diagnosis with high quality, while mitigating operational stress on the operator.

Note that the present invention is not limited to each embodiment described above, and constituent elements can be modified and embodied in the execution stage within the spirit and scope of the invention. The followings are concrete modifications.

(1) Each of the functions described in connection with the above embodiment may be attained by, for example, installing a program for executing the processing in a computer, such as a work station, etc., and expanding the program in a memory. At this time, the program for permitting the computer to execute the processing can be stored in a storage medium, such as a magnetic disk (a floppy disk, a hard disk, or the like), an optical disk (CD-ROM, DVD, Blu-ray disc or the like), and a semiconductor memory, and can be distributed.

(2) The term "processor" used in the foregoing embodiments is, for example, a central processing circuitry (CPU) or a graphics processing circuitry (GPU), or may include the following types of circuitry: application-specific integrated circuitry (ASIC), a programmable logic device (such as a simple programmable logic device (SPLD), or a complex programmable logic device (CPLD), or a field programmable gate array (EPGA)), or the like. The processor realizes its function by reading and executing the program stored in the memory circuitry. Instead of storing a program on the memory circuitry, the program may be directly integrated into the circuitry of the processor. In this case, the function is realized by reading and executing the program integrated into the circuitry. Each processor of the present embodiments is not limited to a case where each processor is configured as single circuitry; a plurality of independent circuits may be combined into one processor to realize the function of the processor. Furthermore, a plurality of constituent elements shown in FIG. 1 may be integrated into one processor to realize the function.

(3) In each of the foregoing embodiments, an example of imaging a two-dimensional image is described. However, the embodiments are not limited to the example, and the embodiments are applicable to a case where a three-dimensional image is taken.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising:
a storing unit configured to store a plurality of images usable as a reference image to be referred to at the time of scanning, the plurality of images includes images corresponding to a plurality of cross sections; and
processing circuitry configured to:
read, when a cross section that needs to be scanned is switched in accordance with a workflow, from the storing unit one or more images registered for each of the plurality of cross sections in advance, the workflow defining a flow of procedures including scanning the plurality of cross sections; and
display the read image as the reference image on a display.

2. The apparatus according to claim 1, wherein the processing circuitry searches the storing unit using a disease name to extract an image related to the disease name, and registers the reference image using the extracted image.

3. The apparatus according to claim 1, wherein the processing circuitry searches the storing unit using past examination information of a same patient to extract at least one of an image scanned for a same area to be examined of the same patient and a reference image used in a past examination, and registers the reference image using the extracted image.

4. The apparatus according to claim 1, wherein the processing circuitry searches the storing unit using at least one of patient information and an area to be examined which are input when performing the workflow to extract an image, and registers the reference image using the extracted image.

5. The apparatus according to claim 1, wherein the plurality of images stored in the storing unit include images used as a good example when scanning each of the cross sections.

6. The apparatus according to claim 5, wherein the plurality of images stored in the storing unit further include images used as a bad example when scanning each of the cross sections.

7. The apparatus according to claim 1, wherein the processing circuitry simultaneously displays the reference image and a current image which is currently being scanned, adjusting display formats of the reference image and the current image.

8. The apparatus according to claim 1, wherein the processing circuitry calculates similarity or dissimilarity between the reference image and a current image which is currently being scanned to determine whether the current image is appropriate or not based on the similarity or the dissimilarity, and outputs a result of the determination in a predetermined format.

9. The apparatus according to claim 8, wherein when the determination indicates that the current image is appropriate, the processing circuitry stores the current image in the storing unit, and when the determination indicates that the current image is inappropriate, the processing circuitry does not store the current image in the storing unit.

10. The apparatus according to claim 1, wherein the processing circuitry stores the reference image along with a current image which is currently being scanned in a predetermined format.

11. The apparatus according to claim 1, wherein the processing circuitry is further configured to register in the storing unit a new image usable as the reference image.

12. A non-transitory computer readable medium storing thereon an ultrasonic image processing program that, when executed by processing circuitry of a computer, causes the computer to,
  store, in a storing unit, a plurality of images usable as a reference image to be referred to at the time of scanning, the plurality of images includes images corresponding to a plurality of cross sections;
  read, when a cross section that needs to be scanned is switched in accordance with a workflow, from the storing unit one or more images registered for each of the plurality of cross sections in advance, the workflow defining a flow of procedures including scanning the plurality of cross sections; and
  display the read image as the reference image on a display.

13. An ultrasonic diagnostic apparatus comprising processing circuitry configured to:
  display a first image and a second image on a display, being arranged side by side, the first image being superimposed with first additional information; and
  store the first additional information in a storing unit, associating the first additional information with the second image as additional information of the second image, in response to an operation by an operator.

14. The apparatus according to claim 13, wherein the first image is an image usable as a reference image to be referred to at the time of scanning.

15. The apparatus according to claim 13, wherein
  the first additional information includes layout information and at least one of a related annotation and a body mark for the first image, and
  the processing circuitry displays the at least one of the annotation and the body mark for the first image, being superimposed on the second image, based on the layout information included in the first additional information.

16. The apparatus according to claim 13, wherein
  the first additional information includes at least one of an annotation and a body mark for the first image, and
  the processing circuitry displays the at least one of the annotation and the body mark at a predetermined location in the second image in accordance with a drag-and-drop operation from the first image to the second image.

17. A medical image processing apparatus comprising processing circuitry configured to:
  display a first image and a second image on a display, being arranged side by side, the first image being superimposed with first additional information; and
  store the first additional information in a storing unit, associating the first additional information with the second image as additional information of the second image, in accordance with a drag-and-drop operation from the first image to the second image.

18. A non-transitory computer readable medium storing thereon an medical image processing program that, when executed by processing circuitry of a computer, causes the computer to,
  display a first image and a second image on a display, being arranged side by side, the first image being superimposed with first additional information; and
  store the first additional information in a storing unit, associating the first additional information with the second image as additional information of the second image, in accordance with a drag-and-drop operation from the first image to the second image.

* * * * *